(12) United States Patent
Bay et al.

(10) Patent No.: US 8,375,054 B2
(45) Date of Patent: Feb. 12, 2013

(54) FINDINGS NAVIGATOR

(75) Inventors: Susanne Bay, Erlangen (DE);
Androniki Begou, Erlangen (DE);
Christoph Braun, Rosenheim (DE);
Sven Kohle, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 879 days.

(21) Appl. No.: 12/078,703

(22) Filed: Apr. 3, 2008

(65) Prior Publication Data
US 2009/0254566 A1  Oct. 8, 2009

(51) Int. Cl.
*G06F 17/30* (2006.01)
(52) U.S. Cl. ...................................................... 707/781
(58) Field of Classification Search .................. 707/781, 707/758, 999.006
See application file for complete search history.

(56) References Cited

U.S. PATENT DOCUMENTS

| | | | |
|---|---|---|---|
| 2005/0060195 A1* | 3/2005 | Bessette et al. | 705/2 |
| 2005/0107689 A1* | 5/2005 | Sasano | 600/425 |
| 2006/0147099 A1* | 7/2006 | Marshall et al. | 382/128 |
| 2007/0140541 A1* | 6/2007 | Bae et al. | 382/131 |
| 2007/0198301 A1* | 8/2007 | Ayers et al. | 705/3 |
| 2009/0143674 A1* | 6/2009 | Nields et al. | 600/437 |
| 2009/0204926 A1* | 8/2009 | Cochrane | 715/781 |
| 2009/0309874 A1* | 12/2009 | Salganicoff et al. | 345/419 |

* cited by examiner

*Primary Examiner* — Kimberly Wilson
*Assistant Examiner* — Mohammed R Uddin
(74) *Attorney, Agent, or Firm* — Harness, Dickey & Pierce, P.L.C.

(57) ABSTRACT

Provided is a method for accessing medical information. The medical information is distributed across data files. The method includes receiving data files relevant to the medical information, selecting a current layout from a plurality of layouts for making the data files accessible, providing previous layout information, referring to a previous layout in which the data file has been acquired, the previous layout information is usable for automatically adapting the current layout to the previous layout, detecting markers associated with the received data files, the markers referring to a location of interest within one of the received data files, adapting the markers of the previous layout to the current layout to mark the same location of interest, and providing access to the medical information in the selected current layout to make browsable the data files and the markers within the data files.

23 Claims, 1 Drawing Sheet

| | Report Nr.▼ | Name▼ | Finder▼ | Value▼ | Image▼ |
|---|---|---|---|---|---|
| ☑ | 1 | Location 1 | LungCare | 23 ml | ▨ |
| ☑ | 2 | Image 1 | Tech | | ▨ |
| ☐ | 3 | Bookmark 1 | Red. | | |
| ☐ | 4 | ROI 1 | Tech | 3.1 cm | ▨ |
| ☐ | 5 | ROI 2 | Tech | 2.4 cm | ▨ |
| ☑ | 6 | Location 2 | LungCare | 20.1 ml | |
| ☐ | 7 | Location 3 | Tech | | | imaging modalities for example computer tomographs (CT), positron emission tomographs (PET) or X-ray units.

FINDINGS NAVIGATOR

FIELD

At least one embodiment of the present invention generally relates to the field of medical informatics or more may specifically relate to information retrieval of medical information for the purposes of medical comparative analysis.

BACKGROUND

The information and communication infrastructure in modern medical facilities are almost exclusively electronic-based these days. Medical information in form of electronic data files for example images files or text files are distributed across picture archive and communication systems (PACS) and hospital information services (HIS) connected either hospital-wide in an intranet network or nationally of even internationally in the familiar internet.

Medical personnel, for example radiologists need to retrieve by retrieval means image files from the PCAS or the HIS for their diagnostic work.

A radiological diagnostic process proceeds roughly along the following lines. In order to reach a diagnostic decision the radiologist must visually examine not only one, but a series of image files.

The image files are available in the well known "Digital Imaging and Communications in Medicine" (DICOM) standard or format. The image files may be slices or parts of higher dimensional volumetric data sets. The volumetric data sets have been acquired from a patient by medical imaging modalities for example computer tomographs (CT), positron emission tomographs (PET) or X-ray units.

In a time-consuming but crucial step, the radiologist is carefully examining by means of a number of dedicated images viewers or simply "viewers" the series of the image files one-by-one in order to locate suspicious features.

The features define locations of interest in some of the image files. The locations of interest along with the radiologist's interpretation thereof constitute a medical "finding" with respect to the image file representing that location of interest. The totality of all findings is then used by the radiologist to either confirm or reject a diagnosis, that is, to reach a diagnostic decision.

Within the course of examining the images files, the radiologist makes notes concerning, for example, measuring information with respect to the locations of interest such as a diameter of a liver shown in the image files. The measurement information, along with other observations such as textual notes and the image files showing the locations of interest can then be compiled into a medical report.

The medical report is then later on possibly transferred to a referring radiologist who wishes to review the image files together with the notes in the medical report, in order to confirm or reject the diagnosis of the radiologist.

However the radiologist may wish to put the image files, the observations and measurement information on hold, in order to discuss the findings with another diagnostician before the radiologist decides to compile the medical report.

The radiological diagnostic process as outlined above normally proceeds in different phases. In a first phase the radiologist normally takes a quick look at all relevant image files just to get a broad overview of the medical information available.

In a second phase the radiologist looks more carefully for the locations of interest in some of the image files, and puts down notes electronically by means of a marking tool, on paper or by using a dictaphone about the observations and the measurement values in order to more accurately describe the locations of interest.

In a third phase the radiologist is then reviewing the image files having the locations of interest in order to for example discuss his or her diagnostic decision on the basis of the findings form the second phases with another radiologist. Also in the third phase the radiologist may whish to be able to quickly retrieve a number of the image files having a particular region of interest and to discuss the respective findings with the other radiologist. Or the radiologist may wish to make a final selection from among the images files suitable to best represent the regions of interest therein and to finally compile the "top 10" of the image files into the medical report.

SUMMARY

It would therefore be desirable for the purposes of medical comparative analysis outlined to have tools available by which the radiologist can temporarily or permanently mark electronically and/or graphically locations of interest by markers within the image files.

It is also desirable to have devices for annotating the locations of interest marked in the image files, such as to dispense with having to put down the observations and measurement information on paper or other external media.

It is also desirable to ease the burden on the radiologist in repeatedly retrieving the image files especially in the second and third phase. In particular the locations of interest marked should be available and visible even though the image file is looked at in the third phase in other layouts or orientations than the ones used in the first or second phase.

This is because the image files as explained are taken from the volumetric data sets. The image viewers used by the radiologist to examine the image files are normally arranged to interface with high performance volume rendering modules operable to generate new slices defining different viewing angles for the same set of original images files or for other image files capable of showing the same location of interest.

Therefore, it would be desirable that the locations of interest marked in one slice corresponding to one frame of reference to be viewable in other slices or image files corresponding to a different slice from a different volumetric data set and/or to different frames of reference.

The image files of other frames of reference have normally been acquired at different times, that is, in different "studies" sometimes using different image acquisition modalities. The images files therefore fall into different categories, that is, the first study, called the baseline study, and the follow up studies, comprising prior studies and the most recent study, called the current study.

It is furthermore desirable that the location of interest in a specific image file is also viewable in other image files from different categories and/or acquired by different imaging modalities—e.g., showing a different tissue contrast—or another imaging modality—and/or another frame of reference. The radiologist is therefore in the position to monitor a progression of a condition of the patient by viewing the region of interest as represented in image files from different categories.

In this case it would be desirable to allow the radiologist to easily access and to make viewable further markers marking the same location of interest in the corresponding image files from a different category than the category of the specific image file in which the radiologist actually set the marker.

The image viewers used in examining the image files allow setting a complex array of layout information whilst examining the image files. There is therefore a need for devices/methods to record the actual settings of the image viewer such as to be able to restore the settings when the radiologist goes back to the image files, either in the same viewer or in a different viewer.

Prior art solutions to the above needs suffer from a number of shortcomings, for the solutions either allow recording the layout information but fail to provide the devices/methods to mark locations of interest taking into account different frames of references and/or image files from different categories.

Other solutions even if though they do allow for marking the locations of interest the fall short of providing the radiologist with the devices/methods to annotate those marked locations of interest with additional information such as measurement values or textual notes.

Finally, there are solutions that allow to the radiologist to set markers for locations of interest in the image files but fail providing a functionality for compiling the image files into the medical report.

There is therefore a need in the art to address all of the above problems and to provide the radiologist with a method, system and devices/methods in order to make medical information distributed across a number of image files available for the purposes of comparative medical analysis.

According to one aspect of at least one embodiment, the present invention relates to a method for providing access to medical information. The medical information is distributed across a plurality of data files and the method comprises:
receiving data files being relevant to the medical information;
selecting a current layout from a plurality of layouts for making the data files accessible;
providing previous layout information referring to a previous layout in which the data file has been acquired. The previous layout information is usable for automatically adapting the current layout to the previous layout;
detecting markers associated with the received data files. The markers refer to a location of interest within one of the received data files, wherein the markers optionally comprise additional information concerning the location of interest;
adapting the markers of the previous layout to the current layout, such as to mark the same location of interest; and
providing access to the medical information in the selected current layout. The medical information comprises the data files and the locations of interest within the data files according to the detected markers, such as to make browsable the data files and the markers within the data files.

The method allows medical personnel, such as a radiologist, easy access in a "reviewing phase" of medical information in data files that have been previously marked in a "reading phase" by the radiologist or by others.

By medical information is meant information that is represented by electronical files such as lab-reports and image files such as slices obtained from volumetric data sets acquired by medical image modalities. The medical information is being used by the radiologist to reach diagnostic decisions on the basis of findings represented by the locations of interest marked.

However, the method according to at least one embodiment of the present invention may also be used for other image post-processing and or recognition systems such as in biology or microscopy.

By "providing access" is meant any device/method suitable to make the medical information represented in the data files available for the radiologist such as to allow examination of the medical information therein. This can be achieved visually or auditory or by other device/method. For example, if the data file is a slice then one way of providing access to the medical information therein is provided by a suitable image viewer into which the slice is loaded and displayed on a suitable display means such as a monitor.

By data files is meant a computer readable representation of the medical information such as a DICOM data file. However, other data file formats may also be used as long as they provide meta-information about the data files such as patient name or number, type of study, information about the acquiring medical modality and as long as they allow pixel information in the data files to be directly addressable. Furthermore, the image data files include information about a frame of reference or the coordinate system used when the image has been acquired.

By current or previous layout information is meant information pertaining to the visual representation of the data files to be used or that have been used when the data file is displayed or have been displayed by the viewer on the monitor. The layout information includes for example the colour encoding, a degree of magnification, panning information and the like. In particular, the layout information pertains to arrangements of different slices shown in the layout side by side, the different slices being obtainable from one or more volumetric data sets.

By locations of interest are meant relevant passages in a lab-report and/or a set of pixels within the data file defining a region, the region representing the medical information in the data files which the radiologist deems useful to illustrate his or her findings.

By markers are meant any suitable device/method by which locations of interest in the data files can be marked or designated such as to make the locations of interest browsable if the radiologist wishes to refer back to those locations of interest in the reviewing phase after the markers have been set. Markers can be set for example by an electronic stylus or a mouse or other pointer that allows to store or record those pixels making up the location of interest and to furthermore provide visual acoustical or other indications with which the locations of interest can be marked. For example, according to one aspect of at least one embodiment of the present invention a mouse is used by the radiologist to circumscribe by circles the locations of interest, the circle being represented in an easily discernable colour.

The location of interest in this case may be taken for example to be a cross-sectional view of the liver taken from the volumetric data set by volume rendering techniques. In this scenario the circle is shown by a conspicuous colour, the circle being superimposed at the pixel coordinates circumscribed, the circle being visible whenever the data file is being viewed by a viewer/user.

According to one aspect of at least one embodiment of the present invention there is/are associated additional information with the locations of interest thus marked. The additional information for example comprises textual notes entered by the radiologist after having marked the regions/locations of interest. This textual information is then shown by popup-menus for example when the respective data file has been loaded into the viewer and the radiologist points the pointer at the marked location of interest. The additional information may also be provided in form of audio files to be automatically replayed while the data file is being viewed or upon issuance of a replay command by having the pointer point to a dedicated "replay" button suitable to issue the command operative in invoking an instance of one of the well-known player applications and loading the audio file thereinto.

This allows the radiologist to dispense with external devices/methods to record additional information in the reading phase and to associate in an intuitive manner the additional information with the correct location of interest.

By "making browsable" is meant the functionality that allows the radiologist to view the locations of interest within the data files by leaping from location of interest to location of interest in a seamless manner, that is, without having to search for the data files having those marked locations of interest. "Making browsable" furthermore includes leaping from different frames of references to another whilst viewing the same location of interest.

Providing access to the medical information according to at least one embodiment of the present invention it therefore suitable for the purposes of medical comparative analysis as it allows the radiologist to rapidly access the marked locations of interest and the additional information associated therewith such as to share this information for example with a colleague for discussing the findings as represented by the marked locations of interest.

According to one aspect of at least one embodiment of the present invention the totality of the received data files and the locations of interest are made browsable by cross-referencing the locations of interest and/or respective data files, the cross-referencing being based on the markers and/or the data files.

According to one aspect of at least one embodiment of the present invention, the cross-referencing is automatically extended to corresponding data files also capable of showing or representing the marked location of interest, such as slices acquired with respect to different frames of reference and/or data files from different categories, that is, data files that have been acquired at different times one the basis of same or different acquisition parameters and or by different imaging modalities.

According to another aspect of at least one embodiment of the present invention, providing access to the medical information comprises toggling between the current layout and the previous layout. This allows for more flexibility and to better adapt to the radiologist's current viewing needs.

According to another aspect of at least one embodiment of the present invention the markers are arranged optionally as bookmarks. The bookmarks are suitable for providing access to the medical information by automatically restoring an application and having the application apply the previous layout to the received data files referred to by the bookmarks. This allows to better help the radiologist viewing the locations of interest in exactly the same setting as in the reading phase. This is useful for better helping the radiologist to recall a relevance of the finding as represented by the location of interest.

According to another aspect of at least one embodiment of the present invention, providing access to the medical information comprises and sorting and/or filtering and/or grouping manually or automatically the received data files according to configurable attributes. The configurable attributes are based on the markers and/or meta-data of the data files and/or the additional information. The meta-data are DICOM objects embedded in the data files.

According to another aspect of at least one embodiment of the present invention there is also displayed the additional information such as measurement values with respect to the marked locations of interest.

This allows the radiologist to have a master-detail-like "bird eye" view on all or parts of the measurements and observations entered in the reading phase without having to load each of the marked data files into the viewer.

According to yet another aspect of at least one embodiment of the present invention the method envisages selecting ones of the browsable data files and compiling the selected ones of the data files and the additional information into a medical report.

According to another aspect of at least one embodiment of the present invention, there is provided a similar method for providing access to medical information without having regard to layout information. This affords for yet greater flexibility, the method being particularly suitable in situations where annotating the data files and their browsability is an issue.

According to another aspect of at least one embodiment of the present invention, there is provided method for consolidating the medical information the data files during the reading phase. The method comprises the steps of setting the markers in respect of the data files and associating the additional information with the markers; and consolidating the medical information by cross-referencing the plurality of the data files, the cross-referencing being based on the markers.

According to another aspect of at least one embodiment of the present invention, the cross-referenced data files comprise further data files, the further data files being also capable of representing the marked locations of interest. This allows the radiologist to easily view in the reviewing phase other data files not actually viewed and examined in the reading phase. The further data files may include data files acquired in the same or different studies with respect to the same or different frame of reference, or from the same or different category.

According to another aspect of at least one embodiment of the present invention there is provided a computer readable medium having computer-executable instructions for performing the methods for the reviewing and reading phase outlined above.

According to another aspect of at least one embodiment of the present invention there is further provided a system to implement the methods according to the present invention.

According to yet a further aspect of at least one embodiment of the present invention there is provided a graphical user interface suitable for use in the system according to the invention and suitable for assisting the radiologist when in reviewing phase.

BRIEF DESCRIPTION OF THE DRAWINGS

The drawings are only for purposes of illustrating embodiments of the invention and are not be construed as to limiting the invention.

DETAILED DESCRIPTION OF EMBODIMENTS OF THE INVENTION

Figures 1, 2:
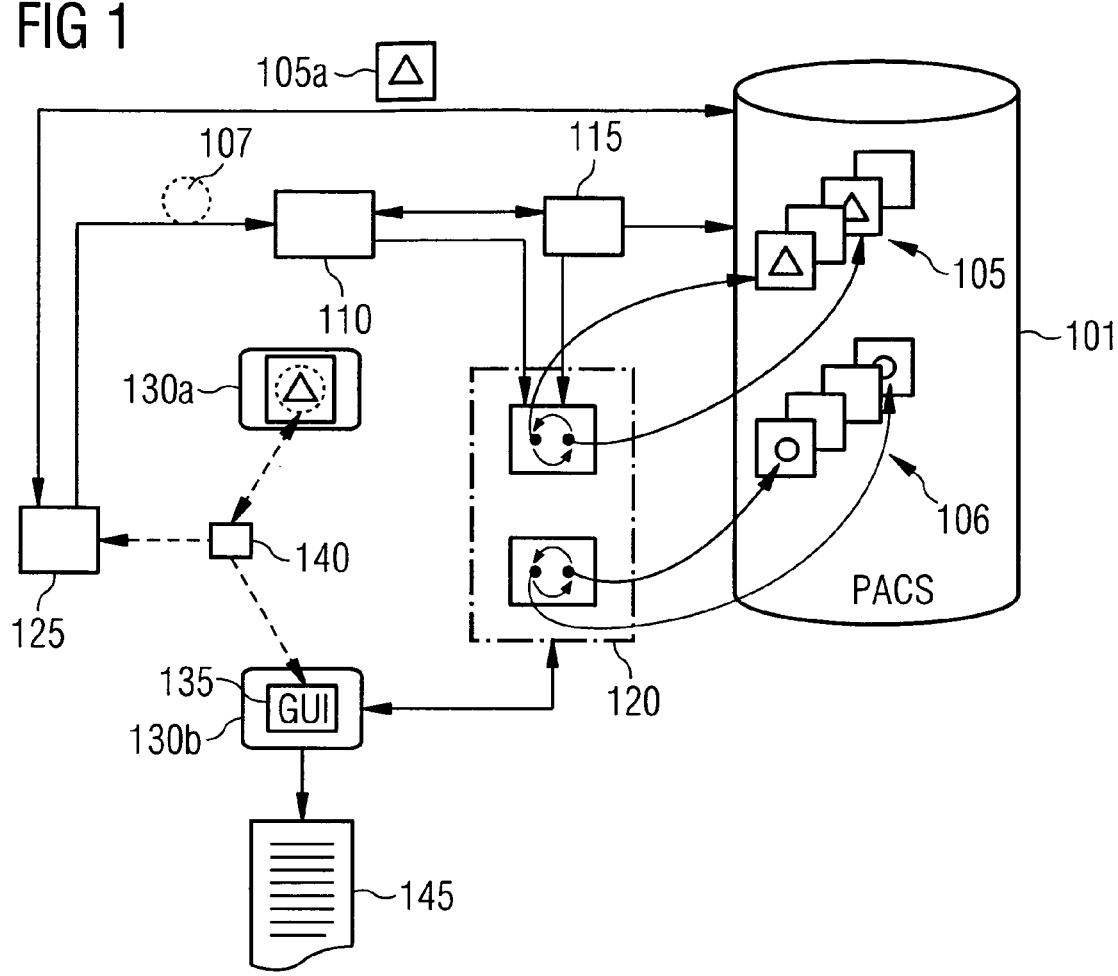
FIG. 1 is a schematic block diagram showing the system according to an embodiment of the invention for providing access to medical information distributed across the plurality of data files.
FIG. 2 is a schematic drawing of graphical user interface according to an embodiment of the invention, allowing browsing the medical information in the data files.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Aspects of a method and a system for accessing medical information are described hereinafter. In the following description, meaning of specific details is given to provide a thorough understanding of embodiments of the invention. One skilled in the relevant art will recognize, however, that the invention can be practiced without one or more of the specific details, or with other methods, modules, entities etc. In other instances, well-known structures, computer related functions or operations are not shown or described in detail, as they will be understood by those skilled in the art.

Reference throughout this specification to "one/an aspect" means that a particular feature, structure or characteristic described in connection with the aspect is included in at least one aspect of at least one embodiment of the present invention. Thus, the appearances of the phrases "according to one aspect" or the like in various places throughout this specification are not necessarily all referring to the same embodiment. Furthermore, the particular features, structures or characteristics may be combined in any suitable manner in one or more embodiments.

FIG. 1 shows an example system for providing access to medical information distributed across a plurality of data files according to an embodiment of the present invention. An embodiment of the invention will be described with particular reference to a special type of data files widely used in the medical field, namely image files and more particularly slices from volumetric data sets. It is to be appreciated, that at least one embodiment of the invention is also applicable to other types of data files such as text files like lab reports and spread sheets or audio files as used in dictations. This invites the person skilled in the art to suitably adapt the components described below without departing form the scope of the invention in a straightforward manner to implement analogous functionalities for use with those other types of data files.

Electronic data files are provided on a picture archive and communication system (PACS) 101. For illustrative purposes the data files are assumed to be medical image data files such as slices 105, 106 representing cross-sectional views of organs of interest. The slices 105, 106 are for example obtained from the volumetric data sets acquired by medical image modalities such as computer tomography (CT) or positron emission tomography (PET) from a patient.

The PACS 101 is connected in the communications network such as a local area network (LAN) or the Internet on the basis of a suitable communication protocols such as HTTP or FTP to a host system 125.

The host system 125 is a computer terminal with input means such as the keyboard and a marking device such as a mouse 140 or an electronic stylus.

According to one aspect of an embodiment of the present invention, there is arranged between the PACS 101 and the host system 125 an intermediate server (not shown). The intermediate server is operative in locally storing the volumetric data slices and includes devices/methods to prepare and/or pre-process the volumetric data files and host application logic systems suitable to send rendered and post-processed slices to the host system 125.

The host system 125 is further connected to output means such as monitors 130a, 130b.

Furthermore, there are provided a referencing module 110 and a referential integrator 115 arranged as software or hardware modules and in communication with the host system 125 and/or the PACS 101.

The referencing module 110 and the referential integrator 115 are running as background processes on the host system 125 and are arranged to monitor an interaction between a radiologist at the host system 125 and a viewer running on the host system 125. The interaction is effected by way of the mouse 140 and or by way of others of the input devices referred to above. The viewer allows the radiologist to load the relevant slice 105a into the viewer and to view the relevant slice 105a on the monitor 130a in a configurable layout setting of the viewer after having downloaded the relevant slice 105a and/or a number of relevant slices from the PACS 101.

The relevant slice 105a is in DICOM format and the radiologist is able to establish the relevance of the slice 105a by querying the PACS 101 by standard database querying tools such as an SQL-interface for DICOM objects represented as meta-information in the relevant slice 105a. DICOM objects are a patient's name, a study ID, a category of the study, modality information and coordinate information such a frame of reference with respect of which the relevant slice has been rendered and or acquired.

The relevant slice 105a may also be a post-processed view of the slices 105, 106, provide by the intermediate server such as 3D-views based on different frames of references having different layout information.

The radiologist then reviews the displayed relevant slice 105a for medical information in form of locations of interest and sets visual or audio markers marking pixels in the relevant slice 105a representative of the locations of interest. It is this interaction of marking locations of interest in the relevant slices 105a viewed on the viewer that is monitored by the referencing module 110. More particularly, it is the coordinates with respect to the DICOM frame of reference of the marked pixels that is monitored. Based on this monitored coordinates the referencing module 110 in communication with the referential integrator 115 are operative in collecting and consolidating the medical information represented by the coordinates of the marked pixels into a file pointer structure 120 such as to make browsable for later reference the marked location of interest.

In general, the operation of the system as shown in FIG. 1 proceeds in two phases, that is, in a "recording phase" and a "reviewing phase".

In the following there is provided a more detailed description of the operation of the system in FIG. 1 by focusing on the functional contributions of the referencing module 110 and the referential integrator 115.

When in reading phase the radiologist basically performs the steps of viewing and marking one-by-one the downloaded relevant slices in a manner outlined above at the example of the relevant slice 105a, using the same or other viewers in medically appropriate layout settings, such as magnification, panning, color encoding etc.

The locations of interest marked represent a type of medical "finding", namely the position of an anatomical feature. There are different types of findings, for example measurement information of the locations of interest, for example the diameter of a cross-sectional view of a liver of the patient as represented in the relevant slice 105a. Other findings relate to the relevant slice 105a as a whole that is they do not relate to a specific single feature in the relevant slice 105a.

The system according to an embodiment of the invention as represented in FIG. 1 allows the radiologist to set different types of markers by the mouse 140 in order to account for the different types of the findings.

The mouse 140 allows the user not only to graphically mark the locations of interest in the relevant slice 105a while viewed on the viewer but also to quantify the location of interest thus marked. The system allows adding measurement information such as length by clicking a specific bottom combination of the mouse 140 while a pointer of the mouse hovers over the marker of the respective location of interest. This generates for example a pop-up window or a tool-tip-like text-field, inviting the radiologist to enter length or width in a suitable scale. Alternatively a known CAD mechanism may be invoked, the CAD mechanism being arranged to perform the measurement automatically.

The markers set by the radiologist may also refer to the image as a whole, for example by mouse-clicking one a frame of the relevant slice 150a viewed. This functionality allows the radiologist to capture the current layout setting chosen to view the relevant slice 150a.

Selecting another bottom combination of the mouse 140 the radiologist can capture not only the current layout setting but also the type of the viewer used to view the relevant slice 105a. This functionality of the markers is also referred to as a bookmark functionality. It allows the user later when referring back to the slice 105 to restore not only the settings but also to automatically load the relevant slice 105a into the same type of viewer as specified by a version number and a vendor type identifier.

A yet other type of button combination of the mouse 140 allows annotating to locations of interest marked by adding textual descriptions whilst keeping the mouse pointer hovering over the marker, the button combination invokes a User interface (UI) to receive a textual note about the findings and its relevance. According to another aspect a microphone is provided that allows the radiologist to record notes in the form of audio files that are then attached to the locations of interest marked.

Information about the graphical representation of the marker used, the coordinate information representing the locations of interest marked by the marker, the layout setting, the measurement values and the additional information in form of textual or audio files are collectively referred to as marker information 107. The marker information is associated to the respective relevant slice 105a.

The referencing module 110 running as a background instance on the host 125 while the radiologist is providing the marker information 107 associates the marker information 107 with a file location path of the relevant slice 105a or the query information used by the radiologist when retrieving or downloading the relevant slice 105a from the PACS 101. The path may be arranged as directory path or a uniform resource locator (URL) but any other identifier suitable to uniquely identify a location of the marked relevant file 105a and that can be used to retrieve the relevant file 105a is within the scope of embodiments of the invention.

The paths and or the query information along with the marker information 107 are then consolidated by reference module 110 into the file pointer structure 120. According to one aspect of an embodiment of the present invention the file pointer structure is arranged as a table in which the path or query information for the relevant slice 105 is associated with the marker information 107 by placing the path and the marker information into a row of the file pointer structure 120.

The marker information 107 is then passed to the referential integrator 115 which is communicating with the reference module 110 in order to ensure that the marker information is also applied if actually viewed to corresponding data files 105, 106 capable of showing for example the same locations of interest as marked in the relevant slice 105a. This is established by for example comparing the coordinate information and the frame of reference in the marker information 107 with the frame of reference DICOM object of other data files 105, 106 as stored in the PACS 101.

The referential integrator is configurable to have the comparison restricted to data files 105, 106 on the PACS 101 from the same patient, the same study ID or category etc.

The functionality provided by the referential integrator 115 allows the same marker information to be available to other slices across which the marked location of interest is visible. If the radiologist for example has marked a location of interest representing a cross-sectional view of a liver this liver is normally extending across a number of slices. The referential integrator 115 ascertains by means of appropriate coordinate transformations that a marker information 107 is accordingly adapted to mark the same location of interest in the other slices from the same or from different volumetric data sets, acquired by the same or by different medical imaging modalities. Those slices that are capable of showing the same location of interest as marked by the marker information 107 are referred to as corresponding slices.

The referential integrator 115 then associates with the row in the table a further table having further rows including paths of all the corresponding slices along with appropriate coordinate transformation information for the marker information 107. The association can be implemented by the known foreign key referencing scheme for tables.

In this way for each other slice retrieved, viewed and marked by the radiologist a corresponding row is added to the table comprising further paths and marker information such as to progressively update the file pointer structure 120.

Upon concluding the reading phase, the file pointer structure 120 is stored either on the host 125 or in the PACS 101 such as to be retrieved at a later stage, when the radiologist whishes to enter the reviewing or demonstration phase.

According to one aspect of an embodiment of the present invention, it is possible for other radiologist upon logging onto the host system 125 to also update the file pointer structure 120. According to this aspect the marker information 107 will further include an ID of the radiologist.

In the reading phase the radiologist wants to refer back to the relevant slices or slice 105a consolidated in the file pointer structure 120 because the radiologist may wish to discuss the findings with a colleague or to prepare a medical report and compile the information consolidated into that report.

To this end the system according to an embodiment of the present invention provides a graphical user interface 135 which the radiologist launches in the monitor 130b on the host system 125.

For illustrative purposes the monitors 130a and 130b have been drawn as two separate monitors but may in practice be in fact one monitor having the viewer run in one window and the graphical user interface 135 in another window. According to another aspect of an embodiment of the present invention, the viewer may still provide views on two different monitors 103a and 130b, the graphical user interface 135 being visible on any of the two monitors 130a, 103b. The system allows the radiologist to configure an behavior in a multi-monitor environment.

The functionalities provided by the graphical user interface 135 according to an embodiment of the present invention are shown in FIG. 2.

The information within the various graphical widgets shown in FIG. 2 are derived from the different rows in file pointer structure 120, that is, from the marker information 107 for each of the relevant slices 105a viewed in the reading phase.

The graphical user interface 135 is a navigation tool according to an embodiment of the present invention that allows the radiologist to browse or to navigate the locations of interest in the relevant slices 105. As the paths of the relevant slices 105 have been consolidated into the rows of the file pointer structure 120 a cross-referencing of the locations of interest and/or the relevant slices has been effected. The graphical user interface 135 interfaces via an underlying translator module (not shown) with the file pointer structure 120 and thus allows commands for functionalities to be described in more detail below to be directly applicable by means of the paths to the relevant slices 105a using the marker information 107.

Each row 201 in FIG. 2 corresponds to marker information 107 associated with the respective relevant slice 105a.

The graphical user interface may take many forms. According to one aspect of the present invention corresponding functionalities associated with different entries in the rows are arranged as widgets and can be constructed in a well-known manner by those skilled in the art from standard widget tool kits such as SUN's SWING system.

The information contained in the column "finder" 202 refers to the ID of the radiologist. It indicates the professional status of the radiologist for example medical or technical staff etc.

In the reviewing phase the radiologist is thought to invoke an instance of a second viewer the second viewer may or may not be different from the viewer used when viewing the relevant slices 105a in the reading phase.

The viewers used by the radiologist on the host system 125 are assumed to be arranged with suitable layout interfaces enabling the viewers to receive or to provide layout information as consolidated in the file pointer structure 120 in the marker information 107 associated with the paths for the relevant slices 105.

By clicking for example an entry in the column "name" 203 in FIG. 2 of the graphical user interface 135 loads the relevant slice 105 by way of the path in the row associated with that entry using a current layout setting of the second viewer. More particularly, current zooming and/or orientation parameters of the views are used and upon loading the relevant slice 105 automatically commence scrolling and/or rotation and/or panning such as to ensure visibility of the marked location of interest along with the marker used in the current layout setting.

Double-click on the same entry would retrieve the previous layout information from the corresponding marker information 107 would reset the layout information to that previous layout information. The radiologist can thus view the slice 105a in exactly the same layout settings as used when the relevant slice 105 was viewed in reading phase. Further clicking effects a toggling between the layouts.

Furthermore the markers, if any, marking the locations of interest are also automatically shown in the relevant slice 105a as viewed using the second viewer in the graphical representation for the marker as specified in the marker information 107.

According to one aspect of an embodiment of the present invention by having a pointer of the mouse 140 hover over the marked locations of interest a pop up window is provided indicating the textual information provided during the reading phase and/or a playback means of the playback data file and the audio file.

According to another aspect of an embodiment of the present invention by having a pointer of the mouse 140 hover over the indicator in the name column in FIG. 2 of graphical user interface 135 another window pops up providing a tabular representation of all the corresponding slices capable of showing the same location of interest. Clicking on a widget representing a path for such corresponding slices initiates retrieving the slice from the PACS 101, loading the slice into the second viewer and to perform a coordinate transformation such as to re-position the marker to mark the same location of interest in the frame of reference as defined by that slice. According to another aspect of an embodiment of the present invention, there are arranged thumbnail widgets, representing all or a configurable group of the relevant slice(s) 105a, the thumbnail widgets allowing enlarging the relevant slice(s) 105a from a thumbnail view to an enlarged view.

The fifth column "value" 20 of the graphical user interface 135 as shown in FIG. 2 provides for convenience measurement information if any of respective location of interest marked.

The sixth column labeled "image" 206 provides thumbnail views of the relevant slices 105a, providing different VRT views of the same location of interest or from different frames of references.

The first column labeled "report" 206 provides the familiar checkbox functionality. This allows the radiologist to select which ones of the slices 105a or the corresponding slices he or she wishes to compile into the medical report, with or with or without the marker information. Checking the appropriate boxes and issuance of a submit command by way of an arranged submit widget (not shown) effects the report to be generated by standard text- and/or graphical-processors, either by incorporating the relevant slices 105a with or without the marker information physically into the report or by merely providing references thereto along with the marker information such as layout information, the textual descriptions of the findings and the measurement values.

According to another aspect of an embodiment of the present invention the graphical user interface 135 provides functionalities via appropriately arranged widgets (not shown) such as filter functionalities for filtering the entries shown in FIG. 2 on the basis of DICOM objects within the respective relevant slices 105a and/or on the basis of the marker information 107.

The radiologist for example wishes to represent on the graphical user interface 135 only those rows 201 referring to selected slices 105a acquired during a specific time span or having certain keywords present in the textual information provided by the radiologist in the reading phase.

According to yet another aspect of an embodiment of the present invention the graphical user interface 135 also provides a drag and drop functionality on the rows 210 shown on the graphical user interface 135 such as to allow the radiologist to group a number of the rows into one row such as to group the referred relevant slices 105a in each of the rows into one entry. This allows the radiologist to simplify the information shown on the graphical user interface 135 according to FIG. 2 and to better structure the findings in the reviewing phase.

The above description of illustrated embodiments of the invention is not intended to be exhaustive or to limit the invention to precise forms disclosed. While specific embodiments of, and examples for, the invention are described herein for illustrative purposes various equivalent modifications are possible within the scope of the invention and can be made without a deviating from the spirit and scope of the invention.

For instance, the description is based on the DICOM format. Alternatively, other formats for medical data may also be used for the method and system according to at least one embodiment of the invention.

Further, the method might be implemented in software, in coded form. Alternatively, it is possible to implement the method according to at least one embodiment of the invention in hardware or hardware modules. The hardware modules are then adapted to perform the functionality of the steps of the method. Furthermore, it is possible to have a combination of hardware and software modules.

These and other modifications can be made to the invention with regard of the above detailed description of example embodiments. The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What we claim is:

1. A method for providing access to medical information, the medical information being distributed across a plurality of data files, the method comprising:
   receiving data files being relevant to the medical information, each of the data files being a 2D image slice used to render a volumetric image layout;
   selecting a current volumetric image layout from a plurality of layouts for making the data files accessible;
   providing previous layout information, referring to a previous volumetric image layout in which the data file has been acquired, the previous layout information being usable for automatically adapting the current volumetric image layout to the previous volumetric image layout;
   detecting markers associated with the received data files, the markers referring to a location of interest within one of the received data files, the markers including additional information concerning the location of interest;
   adapting the markers of the previous volumetric image layout to the current volumetric image layout based on a comparison of coordinate information associated with the marker in order to mark the same location of interest; and
   providing access to the medical information in the selected current layout, the medical information including the data files and the locations of interest within the data files according to the detected markers, to make browsable the data files and the markers within the data files.

2. A method according to claim 1, wherein the making browsable a totality of the received data files and the location of interest is based on at least one of the markers and the data files being cross-referenced.

3. A method according to claim 1, wherein providing access to the medical information includes toggling between the current volumetric image layout and the volumetric image previous layout.

4. A method according to claim 1, wherein the markers are arranged as bookmarks and wherein the bookmarks are suitable for providing access to the medical information by automatically restoring an application and having the application apply the previous layout to the received data files referred to by the bookmarks.

5. A method according to claim 1, wherein access to the medical information is provided for the purposes of a medical comparative analysis of data files and the locations of interest within the data files.

6. A method according to claim 1, wherein providing access to the medical information includes at least one of sorting, filtering, grouping manually and grouping automatically the received data files according to configurable attributes, the configurable attributes being based on at least one of the markers, meta-data of the data files and the additional information.

7. A method according to claim 6, wherein providing access to the medical information further includes displaying at least one of the additional information and the meta-data on which the configurable attributes are based.

8. A method according to claim 1, wherein providing access to the medical information includes displaying the data files, either in the current volumetric image layout or in the previous volumetric image layout, and making browsable the data files and the locations of interest within the data files.

9. A method according to claim 1, further comprising:
   selecting, responsive to a user request, ones of the browsable data files; and
   compiling the selected ones of the data files and the additional information into a medical report.

10. A non-transitory computer readable medium having computer-executable instructions that when executed by a computer cause the computer to perform the following steps:
    receiving data files being relevant to the medical information, each of the data files being a 2D image slice used to render a volumetric image layout;
    selecting a current volumetric image layout from a plurality of layouts for making the data files accessible;
    providing previous layout information, referring to a previous volumetric image layout in which the data file has been acquired, the previous layout information being usable for automatically adapting the current volumetric image layout to the previous volumetric image layout;
    detecting markers associated with the received data files, the markers referring to a location of interest within one of the received data files, the markers including additional information concerning the location of interest;
    adapting the markers of the previous volumetric image layout to the current volumetric image layout based on a comparison of coordinate information associated with the marker in order to mark the same location of interest; and
    providing access to the medical information in the selected current layout, the medical information including the data files and the locations of interest within the data files according to the detected markers, to make browsable the data files and the markers within the data files.

11. A method for consolidating medical information, the medical information being distributed across a plurality of data files, the method comprising:
    setting markers in respect of the plurality of data files, the markers referring at least one of to files and to locations of interest within the data files;
    associating additional information with the markers, the additional information relating to the locations of interest and/or to the data files; and
    consolidating the medical information by cross-referencing the plurality of data files based on applying coordinate information associated with the locations of interest for one of the plurality of the data files to each of a corresponding remaining data files based on the markers.

12. The method according to claim 11, wherein the cross-referenced data files include further data files, the further data files being also capable of representing the marked locations of interest.

13. A non-transitory computer readable medium having computer-executable instructions that when executed by a computer cause the computer to perform the following steps:
    setting markers in respect of the plurality of data files, the markers referring at least one of to files and to locations of interest within the data files;
    associating additional information with the markers, the additional information relating to the locations of interest and/or to the data files; and
    consolidating the medical information by cross-referencing the plurality of data files based on applying coordinate information associated with the locations of interest for one of the plurality of the data files to each of a corresponding remaining data files based on the markers.

14. A system for providing access to medical information, the medical information being distributed across a plurality of data files, the system comprising:
    databases to store the plurality of data files, each of the data files being a 2D image slice used to render a volumetric image layout;

a host system arranged to receive the data files from the databases and for running applications, the applications being suitable for selecting current volumetric image layouts from a plurality of layouts, for making the received data files accessible to a user;

a marking device to set markers in respect of the received data files, the markers referring to locations of interest within the received data files, the marking device allowing associating with and adding to the markers additional information concerning the locations of interest;

a referencing module arranged to cross-reference the marked data files or further data files based on applying coordinate information associated with the locations of interest for one of the marked data files or further data files to each of a corresponding remaining marked data files or further data files based on the markers, the further data files being relevant to the medical information, to make the marked data files and the marked locations of interest browsable;

a referential integrator to adapt the markers of a previous volumetric image layout to the current volumetric image layout, to mark the same location of interest and to automatically cross-reference further data files, the further data files being also capable of representing the marked locations of interest; and a user interface as a navigation tool arranged for browsing at least one of the locations of interest and the cross-referenced data files, the navigation tool being suitable to detect at least one of the markers referring to the locations of interest within the received data files and the additional information.

15. The system according to claim 14, wherein the markers are arranged as bookmarks to additionally refer to a state of the application, the status including information about the previous volumetric image layout, and the including information about the previous volumetric image layout, and the markers being suitable for allowing the navigation tool automatically restoring the application having that state when making the location of Interest accessible to the user.

16. The system of claim 15, wherein the user interface further comprises the functionalities of sorting, filtering and grouping the cross-referenced and marked data files according to the additional information associated with and added to the markers.

17. The system of claim 16, wherein the user interface further comprises a functionality for compiling a medical report based on a selection of the cross-referenced data files, the user interface comprising means for defining the selection.

18. The system of claim 17, wherein the user interface is suitable to display the additional information associated with and added to the markers.

19. A method for providing access to medical information, the medical information being distributed across a plurality of data files, the method comprising:
receiving data files being relevant to the medical information, each of the data files being a 2D image slice used to render a volumetric image layout;
detecting markers associated with the received data files, the markers referring to a location of interest within one of the received data files and the markers including additional information based on coordinate information associated with the markers and concerning the Location of Interest;
providing access to the medical information, the medical information including the data files and the Locations of Interest within the data files according to the detected markers, to make browsable the data files and the markers within the data files.

20. The method according to claim 19, wherein the making browsable a totality of the received data files and the location of interest is based on at least one of the markers and the data files being cross-referenced.

21. The method according to claim 20, wherein the cross-referenced data files include further data files, the further data files being also capable of representing the marked locations of interest.

22. The method according to claim 21, wherein the data files and the further data files are slices from volumetric data sets and wherein the locations of interest are viewable across all the slices.

23. A non-transitory computer readable medium having computer-executable instructions that when executed by a computer cause the computer to perform the following steps:
receiving data files being relevant to the medical information, each of the data files being a 2D image slice used to render a volumetric image layout;
detecting markers associated with the received data files, the markers referring to a location of interest within one of the received data files and the markers including additional information based on coordinate information associated with the markers and concerning the Location of Interest;
providing access to the medical information, the medical information including the data files and the Locations of Interest within the data files according to the detected markers, to make browsable the data files and the markers within the data files.

* * * * *

UNITED STATES PATENT AND TRADEMARK OFFICE
CERTIFICATE OF CORRECTION

| | |
|---|---|
| PATENT NO. | : 8,375,054 B2 |
| APPLICATION NO. | : 12/078703 |
| DATED | : February 12, 2013 |
| INVENTOR(S) | : Bay et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1013 days.

Signed and Sealed this
Second Day of December, 2014

Michelle K. Lee
*Deputy Director of the United States Patent and Trademark Office*